US00PP08654P

United States Patent [19]

VandenBerg

[11] Patent Number: Plant 8,654

[45] Date of Patent: Mar. 22, 1994

[54] CHRYSANTHEMUM PLANT NAMED YELLOW COQUETA

[75] Inventor: Cornelis P. VandenBerg, Salinas, Calif.

[73] Assignee: Yoder Brothers, Inc., Barberton, Ohio

[21] Appl. No.: 935,269

[22] Filed: Aug. 27, 1992

[51] Int. Cl.[5] ..... A01H 5/00

[52] U.S. Cl. ..... Plt./78

[58] Field of Search ..... Plt. 76, 78, 74.1, 82.2

[56] References Cited

U.S. PATENT DOCUMENTS 4,616,099 10/1986 Sparkes ..... 47/58

OTHER PUBLICATIONS

Broertjes, et al., 1980, "A mutant of a mutant of a . . . Irradiation of progressive radiation-induced mutants in a mutation breeding programme with *C. morifolium*", *Euphytica 29: 526–530.*

Gosling, ed., 1979, "The Chrysanthemum Manual-6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by X-rays", Am. Soc. Hort. Sci. Proc., pp. 613–620.

Broertjes, 1966, "Mutation breeding of Chrysanthemums", Euphytica, 15: 156–162.

Dowrick et al., 1966, "The induction of mutations in Chrysanthemum using X- and gamma radiation", Euphytica, 15:204–210.

*Primary Examiner*—Howard J. Locker

*Attorney, Agent, or Firm*—Foley & Lardner

[57] ABSTRACT

A Chrysanthemum plant named Yellow Coqueta particularly characterized by its flat capitulum form; pompon capitulum type; yellow ray floret color, with a dark brown dot in the center of the capitulum; diameter across face of capitulum of 38 to 44 mm when fully opened, when grown as a single stem spray cut mum; photoperiodic flowering response to short days when grown in Salinas, Calif., is 53 to 55 days after start of short days; flowering response in Bogota, Colombia is 70 to 71 days; plant height is 81 to 97 when grown in Salinas with 11 long days prior to start of short days; height is 94 to 112 cm when grown in Bogota with 7 long days prior to start of short days; peduncle length of the first lateral at flowering after removing the apical bud without growth regulator applications is 5 to 15 cm when grown in Salinas, and 10 to 15 cm when grown in Bogota; peduncle length of the fourth lateral at flowering is 10 to 23 days when grown in Salinas, and 15 to 20 cm when grown in Bogota; and excellent tolerance to low night temperatures for bud initiation and flower development.

1 Drawing Sheet

The present invention comprises a new and distinct cultivar of Chrysanthemum, botanically known as *Dendranthema grandiflora,* referred to by the cultivar name Yellow Coqueta.

Yellow Coqueta, identified as 0363 (85-880A02), is a product of a mutation induction program. The new cultivar was discovered and selected by Cornelius P. VandenBerg on Jul. 24, 1989, in a controlled environment in Salinas, Calif., as one flowering plant within a flowering block established as rooted cuttings from stock plants which has been exposed as unrooted cuttings to an X-ray source of 1750 rads in Fort Myers, Fla., on Feb. 9, 1989. The irradiated parent cultivar was the cultivar identified as Coqueta, disclosed in U.S. Plant Pat. No. 7,463, and described as a spray cut mum with a flat capitulum form; a pompon capitulum type; a tricolored capitulum color of white-yellow-brown; diameter across face of capitulum of 40 to 44 mm when fully opened; flowering response period of 53 to 60 days after start of short days in Salinas, Calif., and of 69 to 71 days in Bogota, Colombia; plant height of 89 to 99 cm when grown in Salinas with 6 to 7 long days prior to start of short days, and of 97 to 112 cm when grown in Bogota with 7 long days prior to start of short days; and excellent tolerance to low night temperatures for bud initiation and flower development. The description of Coqueta has a wider range of measurements than the description of Coqueta in the noted plant patent. This is based on the continued flowering trials of Coqueta after writing the application for Coqueta.

The irradiation program resulting in Yellow Coqueta had as its primary objective the expansion of color ranges of the parent cultivar Coqueta. The irradiation program comprises irradiating cuttings of the parent cultivar at irradiation levels of 1500, 1750 and 2000 rads. A total of 1119 cuttings harvested from a total of 225 irradiated plants were planted on May 29, 1989, May 22, 1989 and May 22, 1989, respectively. Of these, 6 initial selections were made, which selections were then revegetated and reflowered. Four consecutive flowering resulted in discarding 5 of the original 6 selections on May 11, 1992. After further testing in Salinas, Calif., and in Bogota, Colombia, the decision was made to introduce the one remaining code as Yellow Coqueta.

The first act of asexual reproduction of Yellow Coqueta was accomplished when vegetative cuttings were taken from the original selection in October 1989 in a controlled environment in Salinas, Calif., by technicians working under supervision of Cornelis P. VandenBerg.

Horticultural examination of controlled flowerings of successive plantings has shown that the unique combination of characteristics as herein disclosed for Yellow Coqueta are firmly fixed and are retained through successive generations of asexual reproduction.

Yellow Coqueta has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Bogota, Colombia under greenhouse conditions which approximate those generally used in commercial greenhouse practice. The low night temperature tolerance was determined in repeated flowerings in Bogota, Colombia.

The following traits have been repeatedly observed and are determined to be basic characteristics for Yellow Coqueta, which, in combination, distinguish this Chrysanthemum as a new and distinct cultivar:

1. Flat capitulum form.
2. Pompon capitulum type.
3. Yellow ray floret color, with a dark brown dot in the center of the capitulum.
4. Diameter across face of capitulum of 38 to 44 mm when fully opened, when grown as a single stem spray cut mum.
5. Photoperiodic flowering response to short days when grown in Salinas, Calif., is 53 to 55 days after start of short days. Flowering response in Bogota, Colombia is 70 to 71 days.
6. Plant height is 81 to 97 cm when grown in Salinas with 11 long days prior to start of short days; height is 94 to 112 cm when grown in Bogota with 7 long days prior to start of short days.
7. Peduncle length of the first lateral at flowering after removing the apical bud without grown regulator applications is 5 to 15 cm when grown in Salinas, and 10 to 15 cm when grown in Bogota. Peduncle length of the fourth lateral at flowering is 10 to 23 cm when grown in Salinas, and 15 to 20 cm when grown in Bogota.
8. Excellent tolerance to night temperatures as low as 5°-19° C. for bud initiation and flower development.

The accompanying photographic drawing is a side view of a single stem cut spray mum of Yellow Coqueta, with the colors being as nearly true as possible with illustrations of this type.

Of the commercial cultivars known to the inventor, the most similar in comparison to Yellow Coqueta is the parent cultivar Coqueta. All traits of Yellow Coqueta are similar to those of Coqueta, except for the ray floret color. Coqueta has a tricolored capitulum color of white-yellow-brown. In several flowering trials in Bogota Yellow Coqueta has been 3 to 5 cm shorter than Coqueta.

In the following description color references are made to The Royal Horticultural Society Colour Chart. The color values were determined on plant material grown as a single stem spray cut mum in Salinas, Calif., on Jun. 30, 1992.

Classification:

*Botanical.*—*Dendranthema grandiflora* cv Yellow Coqueta.

*Commercial.*—Flat pompon cut spray mum.

INFLORESCENCE

A. Capitulum:

*Form.*—Flat.

*Type.*—Pompon.

*Diameter across face.*—38 to 44 mm when fully opened.

B. Corolla of ray florets:

*Color (general tonality from a distance of three meters).*—with a dark brown dot in the center of the capitulum.

*Color (upper surface).*—12A. Brown dot closets to 175B.

*Color (under surface).*—12B.

*Shape of petals.*—Straight, cross-section concave.

C. Corolla of disc florets:

*Color (mature).*—14A, with tips 175B.

*Color (immature).*—12A, with tips 175B.

D. Reproductive organs:

*Androecium.*—Present on disc florets only; scant pollen.

*Gynoecium.*—Present on both ray and disc florets.

PLANT

A. General appearance:

*Height.*—81 to 97 cm when grown in Salinas with 11 long days prior to start of short days; height is 94 to 112 cm when grown in Bogota with 7 long days prior to start of short days.

B. Foliage:

*Color (upper surface).*—147A.

*Color (under surface).*—147B.

*Shape.*—see photograph.

I claim:

1. A new and distinct Chrysanthemum plant named Yellow Coqueta, as described and illustrated.

* * * * *

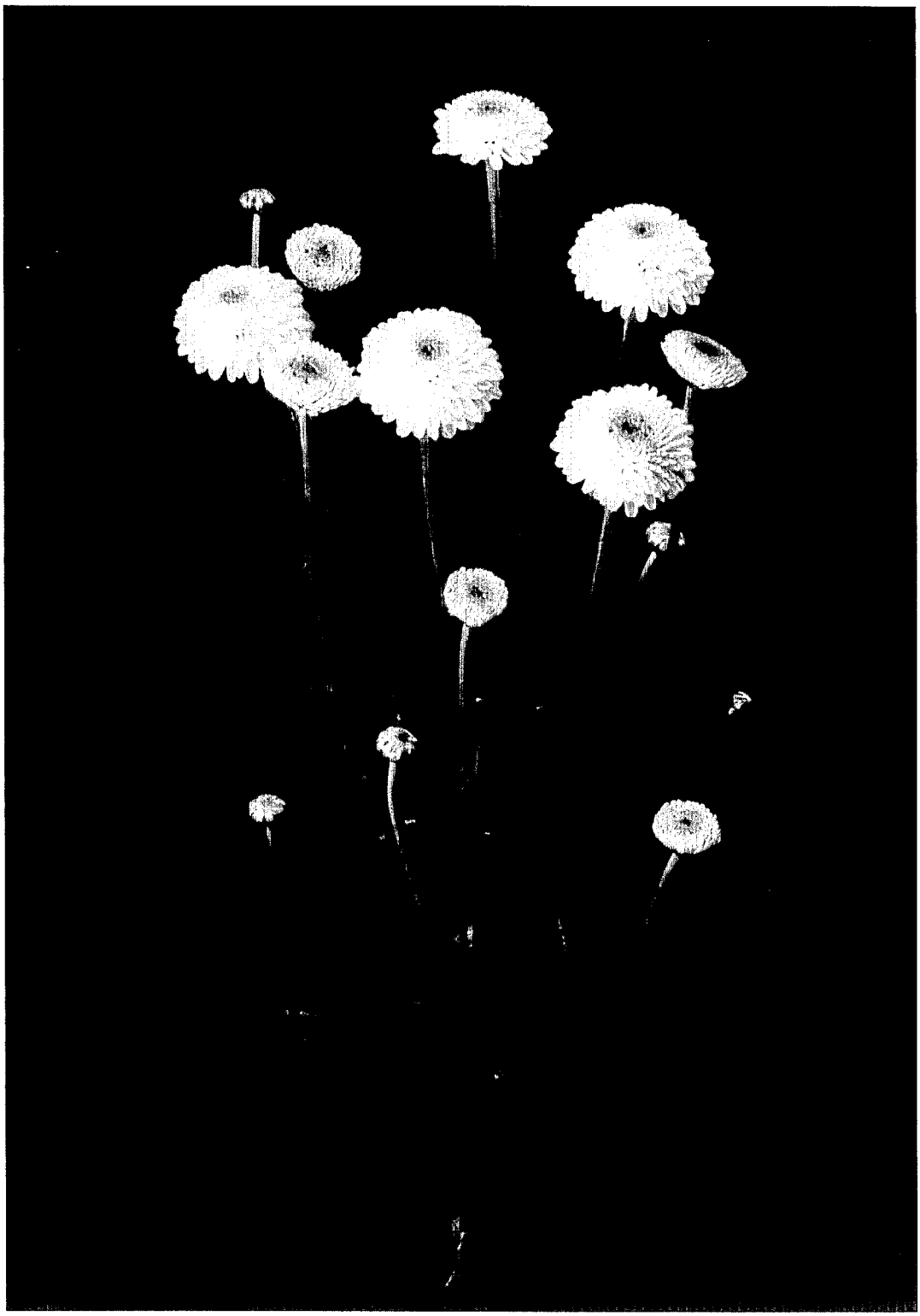

UNITED STATES PATENT AND TRADEMARK OFFICE

CERTIFICATE OF CORRECTION

PATENT NO. : Plant 8,654

DATED : March 22, 1994

INVENTOR(S) : Cornelis P. VANDENBERG

It is certified that error appears in the above-indentified patent and that said Letters Patent is hereby corrected as shown below:

Column 1, line 7, "Cornelius" should read --Cornelis--.

Column 1, line 11, "has been" should read --had been--.

Column 2, line 13, "flowering" should read --flowerings--.

Column 3, line 41, "5 - 19" should read --5 - 10--.

Column 4, line 24, "closets" should read --closest--.

Signed and Sealed this

Eighth Day of November, 1994

*Attest:*

Bruce Lehman

BRUCE LEHMAN

*Attesting Officer*

*Commissioner of Patents and Trademarks*